US00PP25800P2

(12) United States Plant Patent
Osiecki

(10) Patent No.: US PP25,800 P2
(45) Date of Patent: Aug. 11, 2015

(54) *ALOCASIA* PLANT NAMED 'ALO4'

(50) Latin Name: *Alocasia* hybrid
Varietal Denomination: ALO4

(71) Applicant: Marian Osiecki, Marianna, FL (US)

(72) Inventor: Marian Osiecki, Marianna, FL (US)

(73) Assignee: Oglesby Plants International, Inc., Altha, FL (US)

( * ) Notice: Subject to any disclaimer, the term of this patent is extended or adjusted under 35 U.S.C. 154(b) by 159 days.

(21) Appl. No.: 13/986,605

(22) Filed: May 16, 2013

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — Cassandra Bright

(57) ABSTRACT

A new and distinct *Alocasia* cultivar named 'ALO4' is disclosed, characterized by medium to large plant size, very vigorous growth with very early and abundant basal shoot production. Foliage is dark green, with thick, hastate leaf blades, veins surrounded with silver shadowing and light pink petioles with greyed-purple streaks. The new variety is very easy to grow under low and high light conditions as well as low and high temperature conditions and is commercially suitable for 6 to 10 inch pot production from a single tissue culture plantlet. The new variety is an *Alocasia*, typically produced as an ornamental plant.

1 Drawing Sheet

Latin name of the genus and species: *Alocasia* hybrid.
Variety denomination: 'ALO4'.

BACKGROUND OF THE INVENTION

The new cultivar is a product of a planned breeding program. The objectives of the planned breeding program were to develop new *Alocasia* varieties of large size, with fast growth, strong basal shoot production and suitable for 6 to 10 inch commercial pot production. Additionally, the inventor sought interesting foliage and peduncle coloration. The new variety originated from a cross pollination of an unpatented seed parent referred to as 'Aurora' and the pollen parent, an unpatented, unnamed, proprietary variety of *Alocasia lowii*. The crossing was made during May of 2007.

The new variety was discovered by the inventor, Marian Osiecki, a citizen of the US, in September of 2008 in a group of seedlings resulting from the crossing. The new cultivar was found in a commercial greenhouse in Altha, Fla.

Asexual reproduction of the new cultivar 'ALO4' was first performed at a commercial laboratory in Altha, Fla. by tissue culture on Jan. 29, 2009. Subsequent propagation by tissue culture has shown that the unique features of this cultivar are stable and reproduced true to type.

SUMMARY OF THE INVENTION

The cultivar 'ALO4' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALO4.' These characteristics in combination distinguish 'ALO4' as a new and distinct *Alocasia* cultivar:

1. Medium to large size, very vigorous and fast growing plant.
2. Early basal shoot production.
3. Symmetrical growth habit.
4. Dark green, glossy foliage with veins surrounded by wide deep silver shadow.
5. Thick, hastate leaf blades.
6. Attractive pink petioles with distinctive Greyed-Purple markings.
7. Very easy to grow under low and high light conditions as well in low and high temperatures.
8. 'ALO4' is suitable for production in 6" to 10" pots from a single tissue culture plantlet.

PARENT COMPARISON

Plants of the new cultivar 'ALO4' are similar to the unpatented seed parent 'Aurora' in most horticultural characteristics. The new variety however differs in the following characteristics:

1. 'ALO4' is a more vigorous and faster growing plant than 'Aurora'.
2. 'ALO4' is a shorter plant, in a 6" pot it is 40 cm tall, but 'Aurora' is 50-60 cm tall.
3. 'ALO4' is more symmetrical in growth and bigger in diameter compared to 'Aurora'.
4. 'ALO4' is less open in form compared to 'Aurora'.
5. The leaf blades of 'ALO4' are darker, sliver green, thicker and glossier, compared to the light green, less glossy leaf blades of 'Aurora'.
6. Leaf veins of 'ALO4' have a much darker and broader silver shadow than 'Aurora'.
7. The lower side leaf blade of 'ALO4' is burgundy and glossy whereas the lower side leaf blade of 'Aurora' is green and not glossy.

8. Leaf blades of 'ALO4' are oriented horizontally where leaf blades of 'Aurora' are oriented downwardly nodding.
9. Leaf petioles of 'ALO4' are thicker, stronger and shorter compared to the leaf petioles of 'Aurora'.
10. Leaf petioles of 'ALO4' are pink with well marked streaks, whereas the leaf petioles of 'Aurora' are darker pink with very delicate green streaks.

Plants of the new cultivar 'ALO4' are similar to the pollen parent, an unpatented, unnamed, proprietary variety of *Alocasia lowii*, in most horticultural characteristics. The new variety however differs in the following characteristics:

1. 'ALO4' is a shorter plant, in a 6" pot it is 40 to 50 cm tall whereas *A. lowii* is 60 to 70 cm tall.
2. 'ALO4' branches earlier and more abundantly than *A. lowii.*
3. Plants of 'ALO4' are more symmetrical and narrower in diameter compared to *A. lowii.*
4. 'ALO4' is a fuller, less open plant compared to *A. lowii.*
5. The leaf blades of 'ALO4' are smaller than leaf blades of *A. lowii.*
6. The leaf blades of 'ALO4' have less silver color between veins compared to *A. lowii.*
7. Leaf blades of 'ALO4' are oriented horizontally whereas leaf blades of *A. lowii* are oriented downward.
8. Leaf petioles of 'ALO4' are shorter and stronger than leaf petioles of *A. lowii.*
9. 'ALO4' leaf petioles are pink with well marked green or brown streaks whereas *A. lowii* leaf petioles are light green to green color with greenish-brown streaks.

COMMERCIAL COMPARISON

'ALO4' can be compared to the unpatented commercial variety *Alocasia* 'Polly'. Plants of 'Polly' are similar to plants of 'ALO4' in most horticultural characteristics. However 'ALO4' differs from 'Polly' in the following characteristics:

1. 'ALO4' is a more vigorous, taller and faster growing plant than 'Polly'.
2. 'ALO4' is a fuller plant, produces basal shoots earlier and more abundantly compared to 'Polly'.
3. 'ALO4' is a wider and less open plant than 'Polly'.
4. Leaf blades of 'ALO4' are overall larger, with more silver color between veins compared to leaves of 'Polly'.
5. Leaf blades of 'ALO4' are oriented horizontally whereas leaf blades of 'Polly' are oriented downward.
6. 'ALO4' leaf petioles are pink with well marked green or brown streaks whereas 'Polly' leaf petioles are light green to green color with a few very light green streaks.
7. 'ALO4' is more tolerant to disease and stress conditions than 'Polly'.

'ALO4' can be compared to the unpatented species *Alocasia amazonica*. Plants of *Alocasia amazonica* are similar to plants of 'ALO4' in most horticultural characteristics. However 'ALO4' differs from *Alocasia amazonica* in the following characteristics:

1. 'ALO4' is a more vigorous and faster growing plant than *A. amazonica.*
2. 'ALO4' is a fuller plant, produces basal branches much earlier and more abundantly compared to *A. amazonica.*
3. Plants of 'ALO4' are shorter, less spreading, and denser than plants of *A. amazonica.*
4. Mature leaf blades of 'ALO4' are shorter, with more silver color between veins longer than *A. amazonica.*
5. 'ALO4' leaf petioles are pink with well marked green streaks whereas leaf petioles of *A. amazonica* are light green to green color without visible streaks.
6. Leaves of 'ALO4' are oriented horizontally comparing to downwardly nodding leaves of *A. amazonica.*
7. 'ALO4' is more tolerant to disease and stress conditions than *A. amazonica.*

'ALO4' can be compared to the commercial variety *Alocasia* 'ALO1' application Ser. No. 13/986,613. Plants of 'ALO1' are similar to plants of 'ALO4' in most horticultural characteristics. However 'ALO4' differs from 'ALO4' in the following characteristics:

1. Plants of 'ALO4' are shorter and narrower than plants of 'ALO1'. Typically plants of 'ALO4' grow to 48 cm tall and 42 cm in width, whereas similar aged plants of 'AL01' are 65 cm in height and 65 cm wide.
2. Foliage of 'ALO4' is narrower, typically having a range from 11 to 14 cm compared to a typical width of 14 to 19.5 cm for 'ALO1'.
3. The varieties differ in foliage coloration: Mature foliage coloration of 'ALO4' as follows:
   Mature foliage upper side: Near RHS Greyed-Green N189A. RHS Greyed-Green 188C flushing around veins.
   Mature foliage under side: Near RHS Greyed-Purple N186B.

Compared to mature foliage of 'ALO1'
   Mature foliage upper side: Near RHS Green139A, but darker.
   Mature foliage under side: Near RHS Greyed-Purple N186C.
4. Petioles of 'ALO4' are colored primarily Greyed-Purple; petioles of 'ALO1' are colored primarily Greyed-Red.

'ALO4' can be compared to the commercial variety *Alocasia* 'ALO5' application Ser. No. 13/986,604. Plants of 'ALO5' are similar to plants of 'ALO4' in most horticultural characteristics. However 'ALO4' differs from 'ALO5' in the following characteristics:

1. Plants of 'ALO4' are narrower than plants of 'ALO5'. Typically plants of a similar age of 'ALO4' grow to 42 cm in width, whereas similar aged plants of 'AL05' are 60 cm wide.
2. The leaf blade of 'ALO4' is shorter, typically having a range from 28 to 32 cm compared to a typical leaf blade length of 40 to 50 cm for 'ALO5'.
3. 2. The leaf blade of 'ALO4' is narrower, typically having a range from 11 to 14 cm compared to a typical leaf blade length of 16 to 19 cm for 'ALO5'.
4. The petiole of 'ALO4' is colored mainly Greyed-Purple compared to Greyed-Red petioles of 'ALO5'.

BRIEF DESCRIPTION OF THE PHOTOGRAPH

The accompanying photograph in FIG. 1 illustrates in full color a typical plant of 'ALO4' grown in a greenhouse in Altha, Fla. This plant is approximately 6 months old, shown in a 6 inch pot.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'ALO4' plants grown in a climate controlled greenhouse in Altha, Fla., USA. Temperatures ranged from 20° C. to 25° C. at night to 25° C. to 32° C. during the day. No artificial light, photoperiodic treatments were given to the plants. Plants were grown in 80% shade, resulting in approximately 800 to 1200 foot candles of light. Measurements and numerical values represent averages of typical plant types.

Botanical classification: *Alocasia* hybrid 'ALO4'.

PROPAGATION

Root description: Thick, fleshy roots. True rhizomes not observed. Roots approximately 0.4 cm thick, colored near RHS White 155A.

PLANT

Growth habit: Rapid, upright. Basal leaves emerge in clumps.
Plant shape: Upright, petioles and leaves slightly arching out. No stems.
Height: Approximately 48 cm to top of foliar plane.
Plant spread: Approximately 42 cm in a 6 inch pot.
Pot size of plant described: 6 inch.
Growth rate: Rapid.
Branching characteristics: No true branching. Leaves emerge direct from base of plant.
Number of clumps of leaves: 5.
Number of leaves per clump: Average 4 to 12.
Number of leaves per plant: Approximately 20 to 40.
Age of plant described: Approximately 6 months.

FOLIAGE

Leaf:
- *Arrangement*.—Single leaves emerging basally.
- *Largest, mature, fully expanded leaf*.—Length(excluding petiole): Range from 28 to 32 cm. Width: Range from 11 to 14 cm. Shape of blade: Nearly Hastate, with two very deep lobes that angle upward, rather than outward. Aspect: Slightly undulating, mainly flat. Very slightly puckered. Apex: Apiculate. Base: Hastate, with 2 very deep lobes. Average lobe depth 9 cm. Margin: Entire. Appearance: Upper surface glossy. Lower surface glossy. Texture of top surface: Smooth, slightly puckered. Texture of bottom surface: Smooth. Color: Mature foliage upper side: Near RHS Greyed-Green N189A. RHS Greyed-Green 188C flushing around veins. Mature foliage under side: Near RHS Greyed-Purple N186B.

Venation:
- *Type*.—Pinnate.
- *Venation coloration upper side*.—Near RHS Greyed-Green 188C. Center vein RHS Greyed-Green 191B.
- *Venation coloration under side*.—Center vein RHS Yellow-Green 143A, all lateral veins RHS Green 137A.

Petiole:
- *Length*.—Approximate range between 28 and 32 cm.
- *Width*.—At base: Approximately 1.5 cm. At leaf attachment: Approximately 0.7 cm.
- *Color*.—Near RHS Greyed-Purple 186C, densely covered in short stripes near RHS Greyed-Purple N186B. Near leaf attachment, color changes to RHS Yellow-Green 145B, with no stripes approximately 2 cm from attachment point.
- *Strength*.—Very strong.
- *Texture*.—Glabrous.
- *Other*.—Petiole sheath present.

Petiole sheath:
- *Length*.—Approximately 5.0 cm.
- *Width*.—Approximately 1.5 cm.
- *Shape*.—Narrow deltoid.
- *Color*.—Near RHS Greyed-Purple 186D, densely covered in short stripes near RHS N186C.
- *Texture*.—Glabrous.

Immature foliage:
- *Length* (*excluding petiole*).—Range from 10 to 16 cm.
- *Width*.—Range from 5 to 7 cm.
- *Shape of blade*.—Nearly hastate, with two very deep lobes, angled upward, instead of outward. Lobe depth average 30. cm.
- *Aspect*.—Slightly undulating, mainly flat. Very slightly puckered.
- *Apex*.—Apiculate.
- *Base*.—Hastate, with 2 very deep lobes.
- *Margin*.—Entire.
- *Appearance*.—Young foliage upper surface shiny, lower surface glossy.
- *Texture of top surface*.—Smooth.
- *Texture of bottom surface*.—Smooth.
- *Color*.—Young foliage upper side: Near RHS Greyed-Green N189A. Some flushing from veins RHS Greyed-Green 193B. Young foliage under side: Near RHS Greyed-Purple N186C.

Immature foliage venation:
- *Type*.—Pinnate.
- *Venation coloration upper side*.—Near RHS Greyed-Green 193B. Main vein near RHS Yellow-Green 147D.
- *Venation coloration under side*.—Near RHS Yellow-Green 144A.

INFLORESCENCE

Not observed to date.

OTHER CHARACTERISTICS

Disease resistance: Greater resistance than typical of *Alocasia* to *Myrothecium* and leaf *Phytophthora* has been observed.
Drought tolerance and cold tolerance: The new cultivar is a typical *Alocasia*, cold tolerant to approximately 5° to 7° C. and does not tolerate drought.
Fruit/seed production: Not observed.

What is claimed is:

1. A new and distinct cultivar of *Alocasia* plant named 'ALO4' as herein illustrated and described.

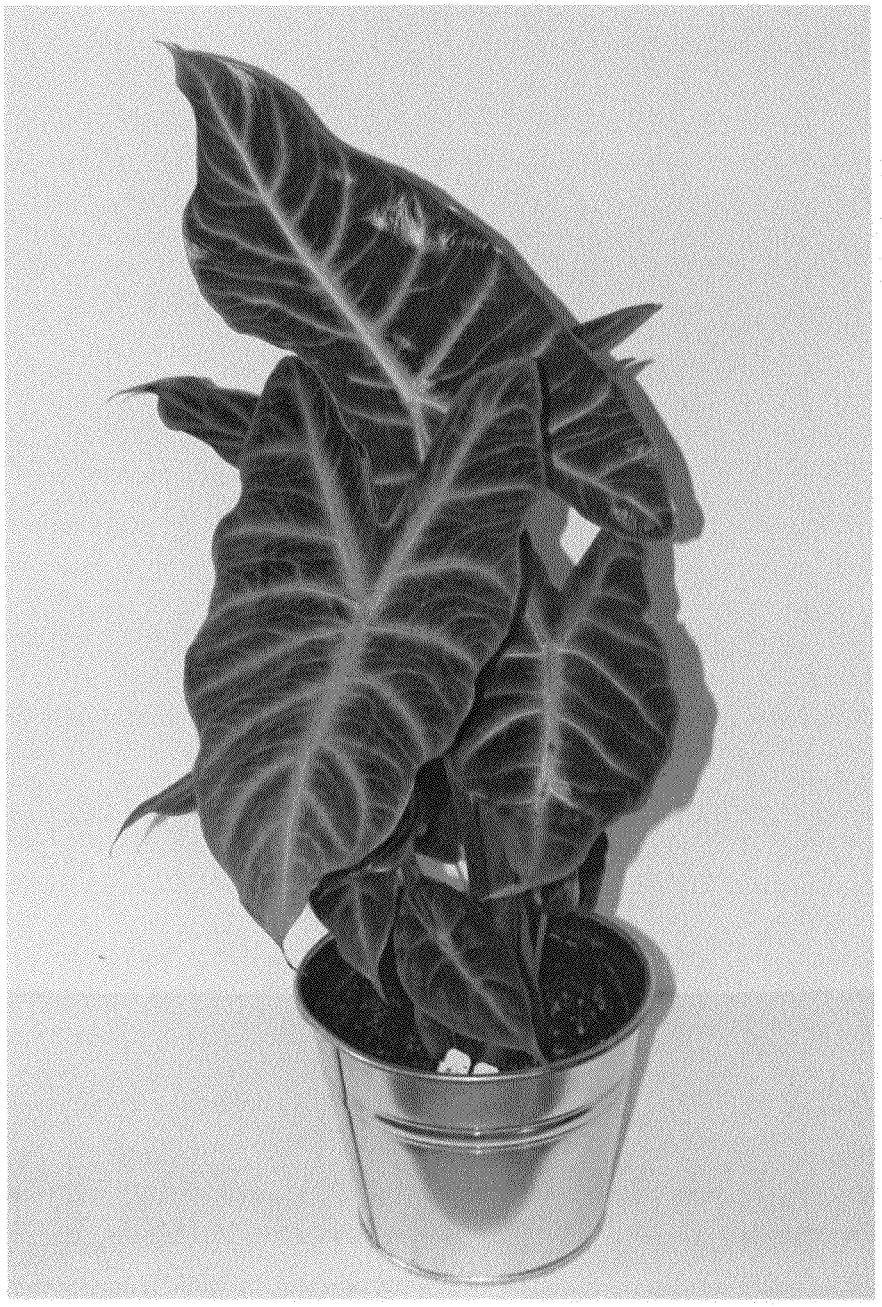

* * * * *